(12) United States Patent
Zierhofer et al.

(10) Patent No.: US 8,046,081 B2
(45) Date of Patent: Oct. 25, 2011

(54) IMPLANTED SYSTEM WITH DC FREE INPUTS AND OUTPUTS

(75) Inventors: Clemens Zierhofer, Kundl (AT); Ingeborg Hochmair, Axams (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 1196 days.

(21) Appl. No.: 11/436,403

(22) Filed: May 18, 2006

(65) Prior Publication Data
US 2007/0270922 A1 Nov. 22, 2007

(51) Int. Cl.
*A61N 1/00* (2006.01)
(52) U.S. Cl. ......................................................... 607/61
(58) Field of Classification Search .............. 607/55–57, 607/61
See application file for complete search history.

(56) References Cited

U.S. PATENT DOCUMENTS

| | | | |
|---|---|---|---|
| 4,261,372 A | 4/1981 | Hansen et al. | 607/137 |
| 4,284,085 A | 8/1981 | Hansen et al. | 607/137 |
| 4,284,856 A | 8/1981 | Hochmair et al. | 607/9 |
| 4,357,497 A | 11/1982 | Hochmair et al. | 607/5 |
| 4,428,377 A | 1/1984 | Zollner et al. | 607/57 |
| 4,532,930 A | 8/1985 | Crosby et al. | 607/57 |
| 4,592,359 A | 6/1986 | Galbraith | 607/57 |
| 4,617,913 A | 10/1986 | Eddington | 607/57 |
| 4,809,712 A | 3/1989 | Kuzma | 607/116 |
| 4,898,183 A | 2/1990 | Kuzma | 607/137 |
| 5,000,194 A | 3/1991 | Van den Honert et al. | 607/137 |
| 5,095,904 A | 3/1992 | Seligman et al. | 607/57 |
| 5,545,219 A | 8/1996 | Kuzma | 623/10 |
| 5,549,658 A | 8/1996 | Shannon et al. | 607/57 |
| 5,571,148 A | 11/1996 | Loeb et al. | 607/57 |
| 5,578,084 A | 11/1996 | Kuzma et al. | 623/10 |
| 5,601,617 A | 2/1997 | Loeb et al. | 607/56 |
| 5,609,616 A | 3/1997 | Schulman et al. | 607/57 |
| 5,645,585 A | 7/1997 | Kuzma | 623/10 |
| 5,649,970 A | 7/1997 | Loeb et al. | 607/57 |
| 5,741,314 A | 4/1998 | Daly et al. | 607/60 |
| 5,749,912 A | 5/1998 | Zhang et al. | 607/57 |
| 5,824,022 A | 10/1998 | Zilberman et al. | 607/57 |
| 5,876,443 A | 3/1999 | Hochmair et al. | 623/10 |
| 5,891,183 A | 4/1999 | Zierhofer | 607/57 |
| 5,938,691 A | 8/1999 | Schulman et al. | 607/57 |
| 5,983,139 A | 11/1999 | Zierhofer | 607/56 |
| 5,997,524 A | 12/1999 | Burbank et al. | 604/506 |
| 5,999,859 A | 12/1999 | Jolly | 607/137 |
| 6,175,767 B1 * | 1/2001 | Doyle, Sr. | 607/57 |
| 6,181,969 B1 | 1/2001 | Gord | 607/59 |
| 6,195,585 B1 | 2/2001 | Karunasiri et al. | |
| 6,231,604 B1 | 5/2001 | Von Ilberg | 623/10 |
| 6,259,951 B1 | 7/2001 | Kuzma et al. | 607/57 |
| 6,309,410 B1 | 10/2001 | Kuzma et al. | 607/137 |
| 6,324,429 B1 | 11/2001 | Shire et al. | |
| 6,348,070 B1 | 2/2002 | Teissl et al. | 623/11 |
| 6,377,849 B1 | 4/2002 | Lenarz et al. | 604/21 |
| 6,556,870 B2 | 4/2003 | Zierhofer et al. | 607/57 |
| 6,597,525 B2 | 7/2003 | Zierhofer | 607/57 |
| 6,600,955 B1 | 7/2003 | Zierhofer | 607/57 |
| 6,661,363 B2 | 12/2003 | Zierhofer | 341/143 |

\* cited by examiner

*Primary Examiner* — Eric D. Bertram
(74) *Attorney, Agent, or Firm* — Sunstein Kann Murphy & Timbers LLP

(57) ABSTRACT

An implantable electronic system is described. An implantable power supply includes multiple power input ports for receiving an externally generated power supply signal, and multiple power output ports for developing a detected power signal. An implantable prosthetic processing module includes multiple prosthetic processing input ports connected by wire to the power output ports for receiving the detected power signal, and multiple prosthetic processing output ports for developing a prosthetic stimulation signal output for electrically stimulating target neural tissue. Each of the multiple ports is adapted to operate without developing a dc potential.

11 Claims, 7 Drawing Sheets

Skin

Implanted system comprising a supply system and a system integrated on a single chip Control signals φ₁(t) and φ₂(t) and output signal u_P(t)

General configuration of a single-chip system

Full wave rectifier composed of MOS-transistors switched as diodes

Full wave rectifier composed of active MOS-transistors

IMPLANTED SYSTEM WITH DC FREE INPUTS AND OUTPUTS

FIELD OF THE INVENTION

The invention relates to implantable electronic systems, and specifically to the power supply systems of such devices.

BACKGROUND ART

A very general active implantable system might look as depicted in FIG. 1. It consists of two implanted subsystems, a supply system 101, and a single chip processing system 102. The supply system 101 may contain input contacts 103 and 104, and output contacts 107 and 108. The input contacts are typically connected to each other via an inductive coil 105 (having an associated inductance $L_2$). Implanted coil 105 might be inductively coupled to another external coil 106 (having its own inductance $L_1$), which is positioned outside the body. Both coils form a weakly coupled transformer with external coil 106 as the primary winding and implanted coil 105 as the secondary winding. This allows a transfer of electrical energy via the intact skin surface (transcutaneous power transfer). The supply system 101 converts a radio-frequency (rf) signal $u_2(t)$ to an appropriate internal signal $u_p(t)$ at the power supply output contacts 107 and 108. The power supply output contacts 107 and 108 are connected to the processing system input contacts 109 and 110 by isolated wires 111 and 112. Signal $u_p(t)$ may supply the processing system 102 with both energy and information. Neglecting the electrical impedance of wires 111 and 112, signal $u_p(t)$ also appears between processing system input contacts 109 and 110.

The processing system 102 typically performs particular measurement and/or active stimulation tasks, e.g., measurement of bio-electrical signals, sensing of chemical substances, and/or applying electrical signals to the surrounding tissue. Signals are sensed and/or applied by means of a set of electrodes 113. One special property of the processing system 102 is that, due to very restrictive spatial requirements, the whole functionality may be integrated on a single electronic chip. In contrast to the supply system 101 where electronic circuits might be protected against body fluids by means of a hermetically sealed package, the processing system 102 is typically protected only by various thin passivation layers (e.g., oxides). In addition, there may be no room for additional electrical components such as external diodes or discrete capacitors.

One specific example of a system as set forth in FIG. 1 may be a retinal prosthesis such as is described in Margalit E, Maia M, Weiland J D, Greenberg R J, Fujii G Y, Torres G, Piyathaisere D V, O'Hearn T M, Liu W, Lazzi G, Dagnelie G, Scribner D A, de Juan E, and Humayun M S, *Retinal Prosthesis For The Blind,* Survey of Ophthalmology, Vol. 47, No. 4, July-August 2002 (incorporated herein by reference). In that system, the processing system chip is located either on the surface of the inner retina (epiretinal approach) or in the subretinal space (subretinal approach). Typically, the size of the processing chip is some square millimeters, and the thickness is some tens of microns. For protection, the processing chip is covered by a several layers of light-transparent materials. The processing chip may include an array of subunits where each subunit includes a photodiode, an analog amplifier and a stimulating electrode. These subunits may be designed to convert the light energy (photons) from images into electrical impulses to stimulate the remaining functional cells of the retina.

Unfortunately, early hopes that such an implanted data processing chip could be powered solely by incident light without the use of external supply were not realized. Thus, the retinal processing chip has to be connected to a supply system providing power and control signals. For example, the supply system could be implanted in the area behind the ear, similar to a cochlear implant as described, for example, in Waltzman S B and Cohen N L, *Cochlear Implants,* ISBN 0-86577-882-5, Thieme New York, 2000 (incorporated herein by reference). Such a supply system could contain rechargeable batteries which could be recharged (if required) using a transcutaneous inductive link as described, for example, in Zierhofer C M and Hochmair E S, *High-Efficiency Coupling-Insensitive Power And Data Transmission Via An Inductive Link,* IEEE-Trans. Biomed. Eng. BME-37, pp. 716-723, July 1990 (incorporated herein by reference). Thus, a system configuration as shown in FIG. 1 is obtained.

SUMMARY OF THE INVENTION

A representative embodiment of the present invention includes an implantable electronic system. An implantable power supply includes multiple power input ports for receiving an externally generated power supply signal, and multiple power output ports for developing a detected power signal. An implantable prosthetic processing module includes multiple prosthetic processing input ports connected by wire to the power output ports for receiving the detected power signal, and multiple prosthetic processing output ports for developing a prosthetic stimulation signal output for electrically stimulating target neural tissue. Each of the multiple ports is adapted to operate without developing a dc potential.

In further embodiments, the power supply and/or the prosthetic processing module may be in a non-hermetic, humidity resistant package. At least one of the multiple ports may include a disconnectable connector to allow wires to be easily attached to and detached from the plurality of ports.

In various embodiments, the externally generated power supply signal is a radio frequency signal, for example, developed by an implanted receiving coil. The externally generated power supply signal may contain both energy and information.

Some embodiments may further include at least one pair of output ports for producing a received power signal without developing a dc potential between the output ports. A processing module may receive the received power signal. The processing module may be located within the hermetically sealed package. The processing module may be coupled to a tissue interaction element, for example, a stimulation electrode element, or a tissue sensor element.

Embodiments also include an implantable prosthesis system including an implantable electronic system according to any of the foregoing. A specific system may be a cochlear prosthesis system or a retinal prosthesis system.

Another embodiment includes an implantable electronic system having a single implantable non-hermetic, humidity resistant package containing a power supply and a prosthetic processing module. The power supply includes power input ports for receiving an externally generated power supply signal. The prosthetic processing module has prosthetic processing output ports for developing a prosthetic stimulation signal output for electrically stimulating target neural tissue. Each of the ports is adapted to operate without developing a dc potential.

In further such embodiments, the package may be a single chip package. At least one of the ports may include a disconnectable connector to allow wires to be easily attached to and detached from the ports. The externally generated power supply signal may be a radio frequency signal. The externally generated power supply signal may be developed by an implanted receiving coil and/or may contain both energy and information.

Embodiments also include an implantable prosthesis system including an implantable electronic system according to any of the above embodiments. For example, the system may be a cochlear prosthesis system or a retinal prosthesis system.

DETAILED DESCRIPTION OF SPECIFIC EMBODIMENTS

Figure 1:
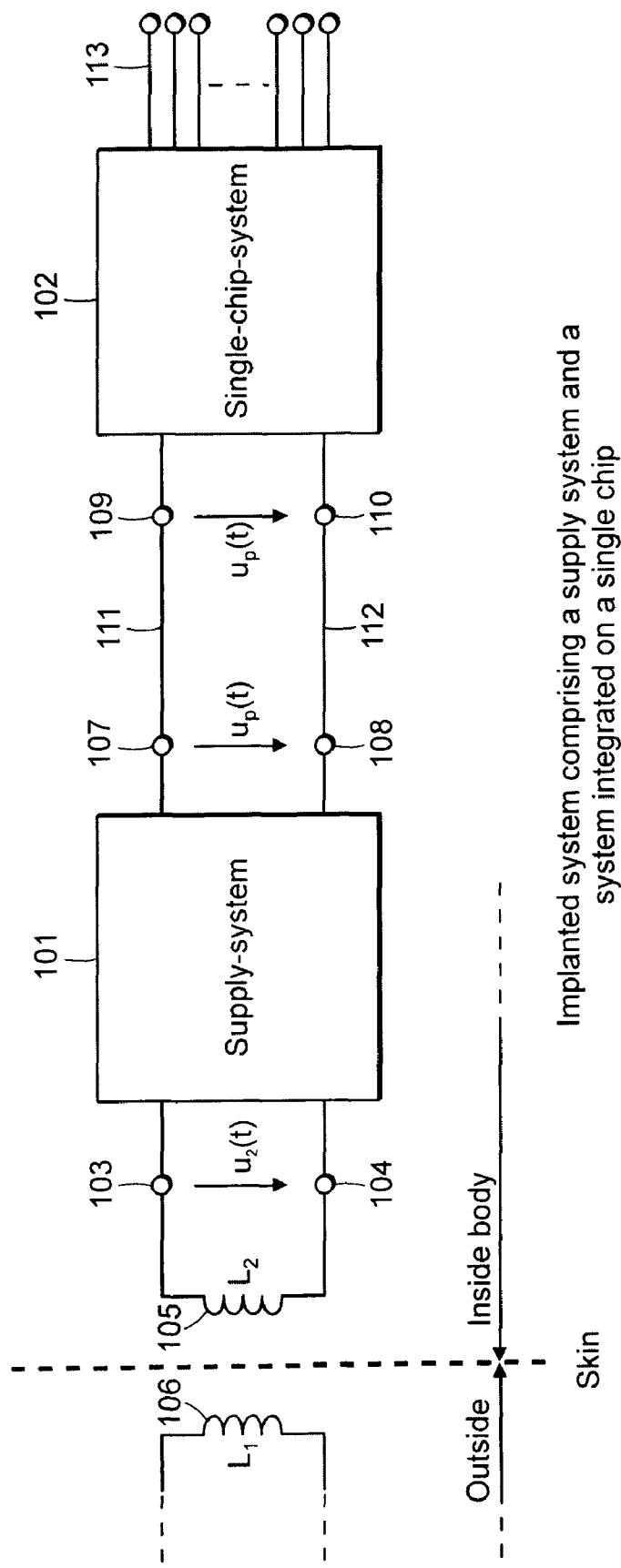
FIG. 1 shows functional elements of a generic implanted electronic system.

Embodiments of the present invention are directed to an implantable electronic system which does not develop a dc potential between its ports. For example, the implantable electronic system may be a supply system and single chip processor as shown in FIG. 1 with dc free input and output contacts. The supply system and/or the single chip processor may be contained within a non-hermetic, humidity resistant package, which is gas permeable when implanted, but resists being affected by the humid biologically active implanted environment. In other specific embodiments, the humidity resistant package may be hermetically sealed.

Figure 2:
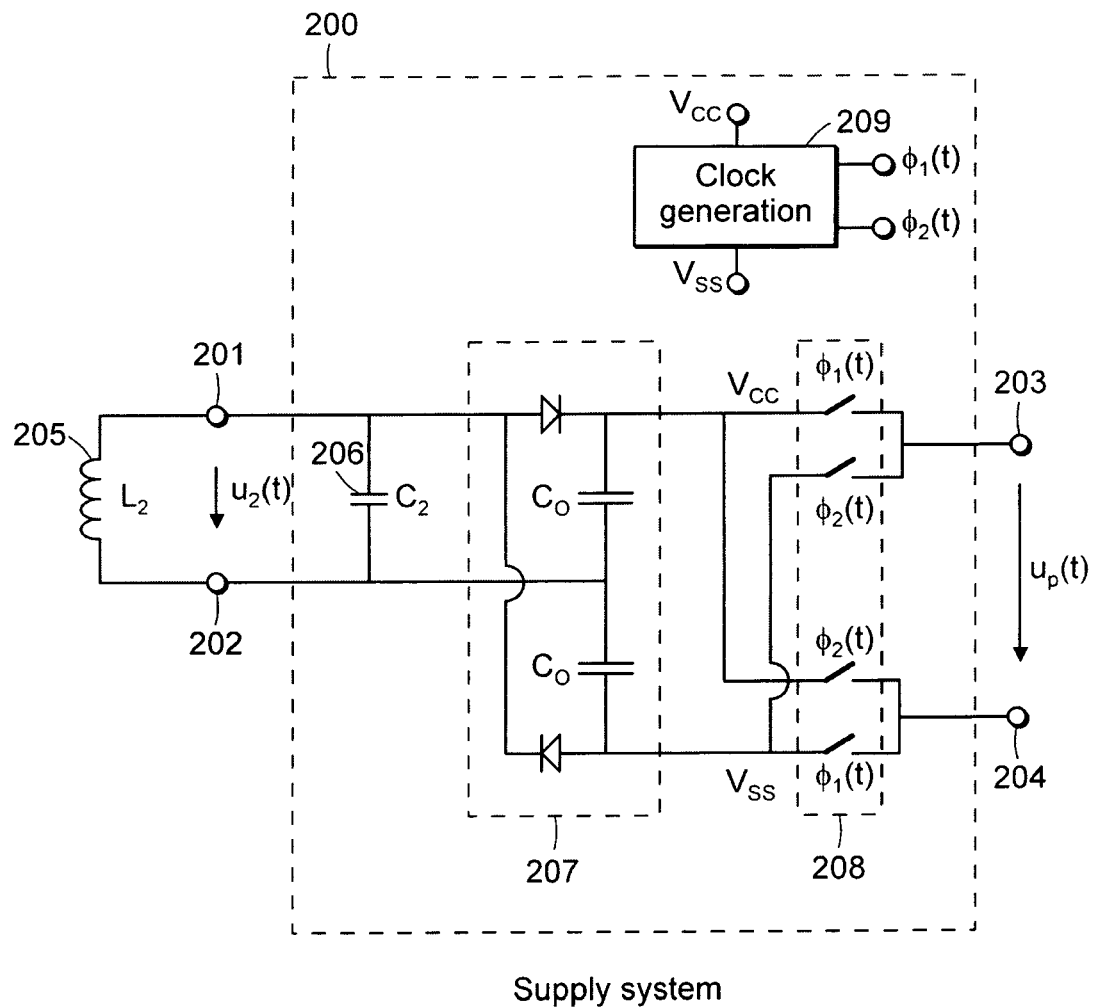
FIG. 2 shows functional elements of a supply system according to one embodiment of the present invention.

FIG. 2 shows an embodiment in of an implantable power supply which has dc-free input and output contacts. Supply input contacts 201 and 202, supply output contacts 203 and 204, and supply input coil 205 are outside the humidity resistant package 200. Implanted supply input coil 205 (having an inductance $L_2$) and supply input capacitor 206 (having a capacitance $C_2$) represent a parallel tuned circuit to receive an externally generated radio-frequency (rf) power signal $u_2(t)$. Assuming that the supply input coil 205 is ideal, there is no dc potential developed between the input contacts 201 and 202. Signal $u_2(t)$ is full-wave rectified and smoothed by a rectifier circuit 207 which includes two diodes and two capacitors (capacitances $C_0$). For sufficiently large capacitances $C_0$, the resulting voltages $V_{CC}$ and $V_{SS}$ are dc-like potentials. The supply system also contains a clock generator 209 which generates non-overlapping clock signals $\phi_1(t)$ and $\phi_2(t)$. These clock signals $\phi_1(t)$ and $\phi_2(t)$ control switches within a switching matrix 208.

Figure 3:
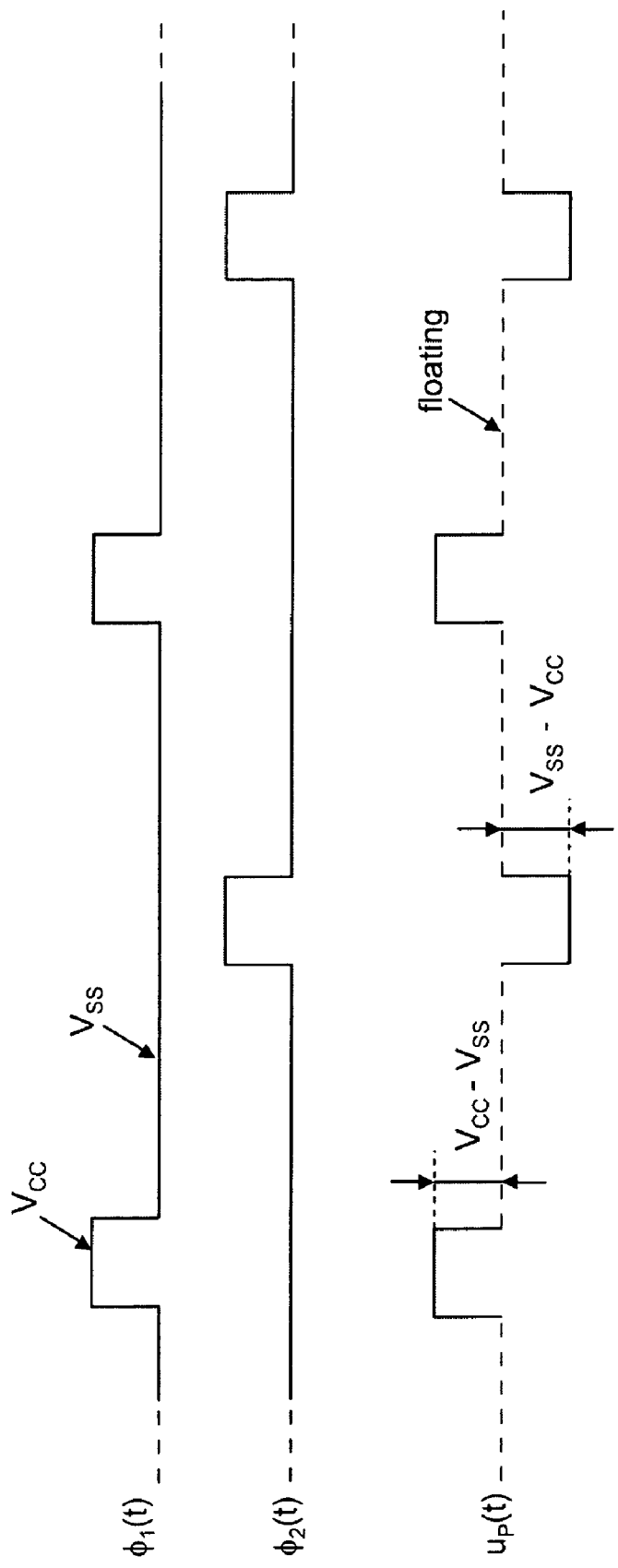
FIG. 3 shows various signals associated with the system in FIG. 2.

As shown in FIG. 3, during the periods when $\phi_1(t)=V_{CC}$ and $\phi_2(t)=V_{SS}$, voltages $V_{CC}$ and $V_{SS}$ respectively are connected to the supply output contacts 203 and 204 such that $u_p(t)=V_{CC}-V_{SS}$. Vice versa, during $\phi_1(t)=V_{SS}$ and $\phi_2(t)=V_{CC}$, it follows that $u_p(t)=V_{SS}-V_{CC}$. For $\phi_1(t)=V_{SS}$, and $\phi_2(t)=V_{SS}$, the supply output contacts 203 and 204 are floating, i.e., they have no defined electrical potential. If the mean duration of state $\phi_1(t)=V_{CC}$ is equal to the mean duration of state $\phi_2(t)=V_{CC}$, then supply output contacts 203 and 204 have no dc-potential between each other. In addition, there is no dc-voltage with respect to the supply input contacts 201 and 202, despite the diode voltage drops in rectifier 207. In the case where voltage $u_p(t)$ has no floating phase and states $\phi_1(t)=V_{CC}$ and $\phi_2(t)=V_{CC}$ for equal durations, an almost glitch-free dc-supply voltage for the signal processing stage of the chip is generated. In specific embodiments, the developed signal may contain both energy and information.

Figure 4:
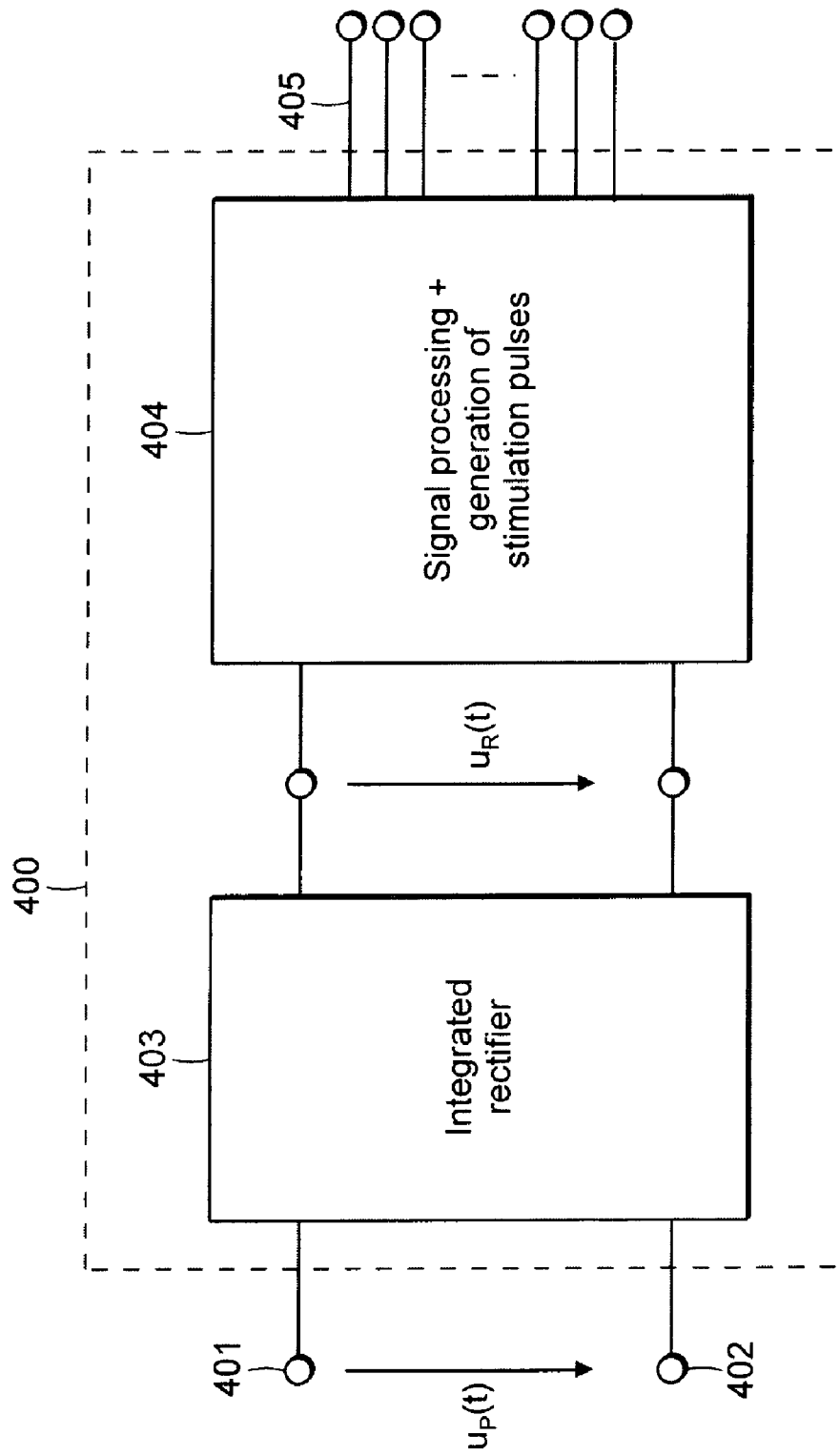
FIG. 4 shows the general configuration of one specific embodiment of a single chip processor.

An example of a single chip implantable electronic system is shown in FIG. 4. The single processor chip 400 is protected against humidity such as body fluids by one or more passivation layers. Processor chip 400 includes an integrated rectifier 403 and a subsequent processing stage 404 implementing functionality for signal processing and/or stimulation pulse generation. Proper operation of processing stage 404 relies on a power supply voltage with one particular polarity such as is produced by the integrated rectifier 403. For an ideal rectifier if the input signal is defined, then the rectifier output signal is equal in magnitude to that of the input signal, i.e., $u_R(t)=|u_P(t)|$. If the input signal $u_p(t)$ is generated by a supply system such as the one shown in FIG. 2, then $u_R(t)=V_{CC}-V_{SS}$ during the periods when $u_P(t)$ is non-floating.

Figure 5:
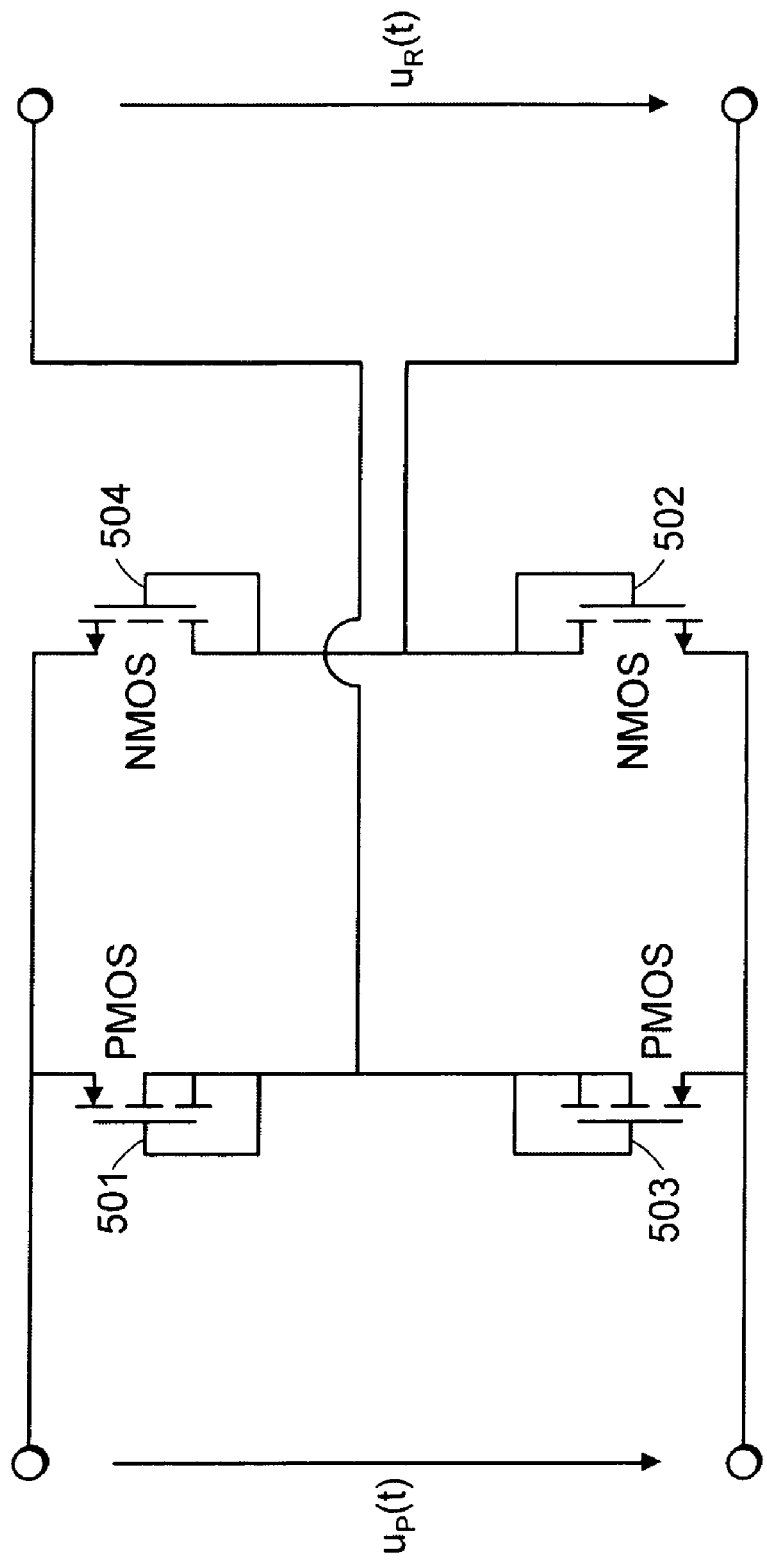
FIG. 5 shows an example of a full wave rectifier composed of MOS-transistors switched as diodes.
Figure 6:
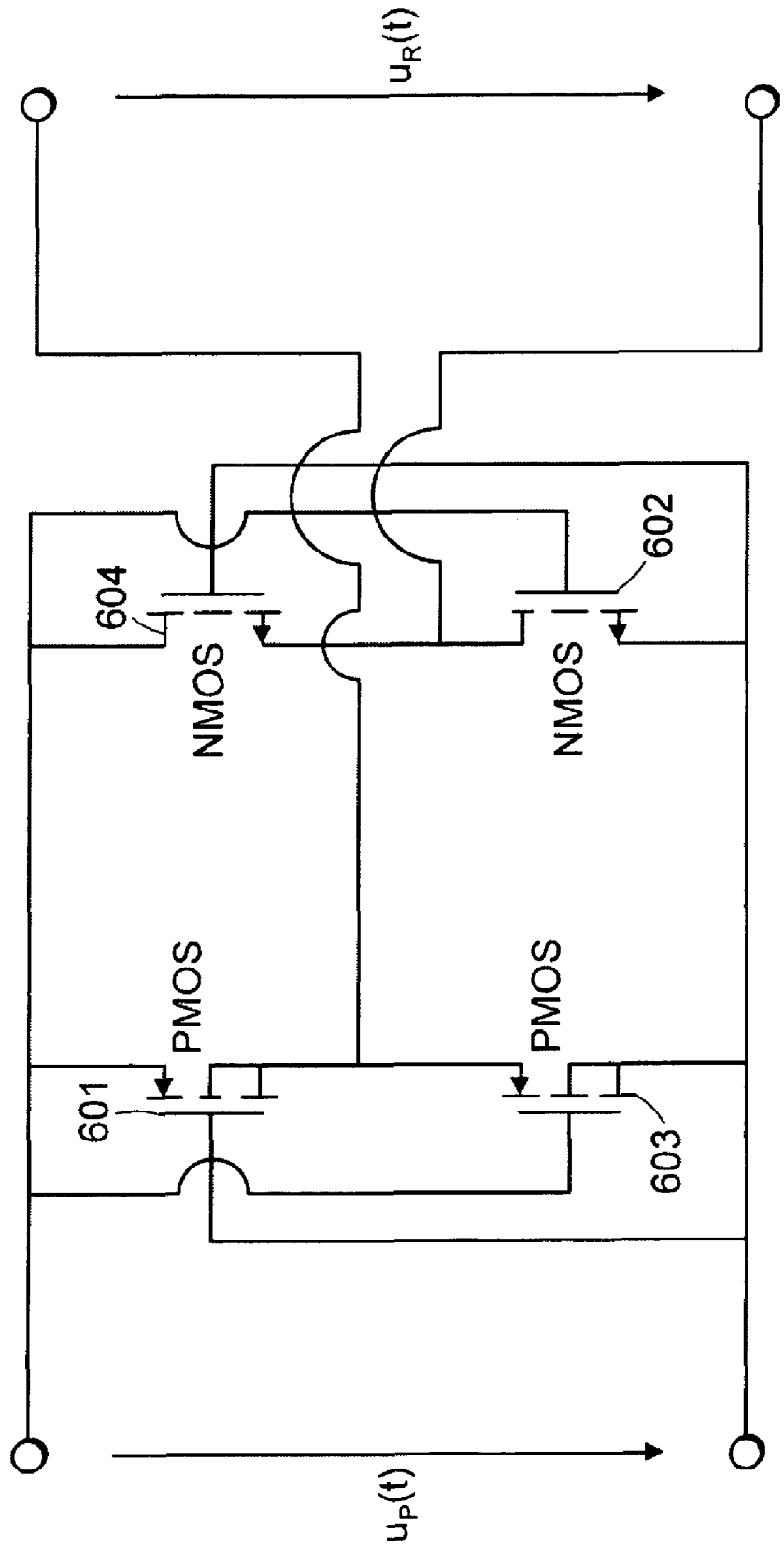
FIG. 6 shows an example of a full wave rectifier composed of active MOS-transistors.

Examples of integrated rectifiers are shown in FIGS. 5 and 6. The rectifier depicted in FIG. 5 represents a textbook approach where MOS-transistors 501, 502, 503, and 504 are switched as diodes, i.e., the gates are connected to the drains, respectively. While this approach is very well suited for integration, one disadvantage is that the voltage drops between sources and drains across the MOS-transistors, $U_{SD} \approx 1-2V$, occur respectively. Thus the output voltage is diminished by $2U_{SD}$, i.e., $u_R(t)=|u_P(t)|-2U_{SD}$. For low voltage applications, this reduction might be a significant consideration.

The approach shown in FIG. 6 also utilizes MOS-transistors and thus is well suited for integration, but it avoids large voltage drops across transistors as described in U.S. provisional patent application 60/697,624, filed Jul. 8, 2005, incorporated herein by reference. There are two PMOS-transistors 601 and 603, and two NMOS transistors 602 and 604, which are operated as ON/OFF-switches. Standard CMOS-technology can be used. The gates of the transistors are directly connected to the input voltage rails. For sufficient magnitude of the input voltage difference, it is ensured that $u_R(t) \approx |u_P(t)|$. The four transistors should be sufficiently large so that there is only a small voltage drop during the switch ON-states. If the voltage drops are too large (typically, larger than about 0.7V), then parasitic substrate PN-diodes tend to get conductive.

Figure 7:
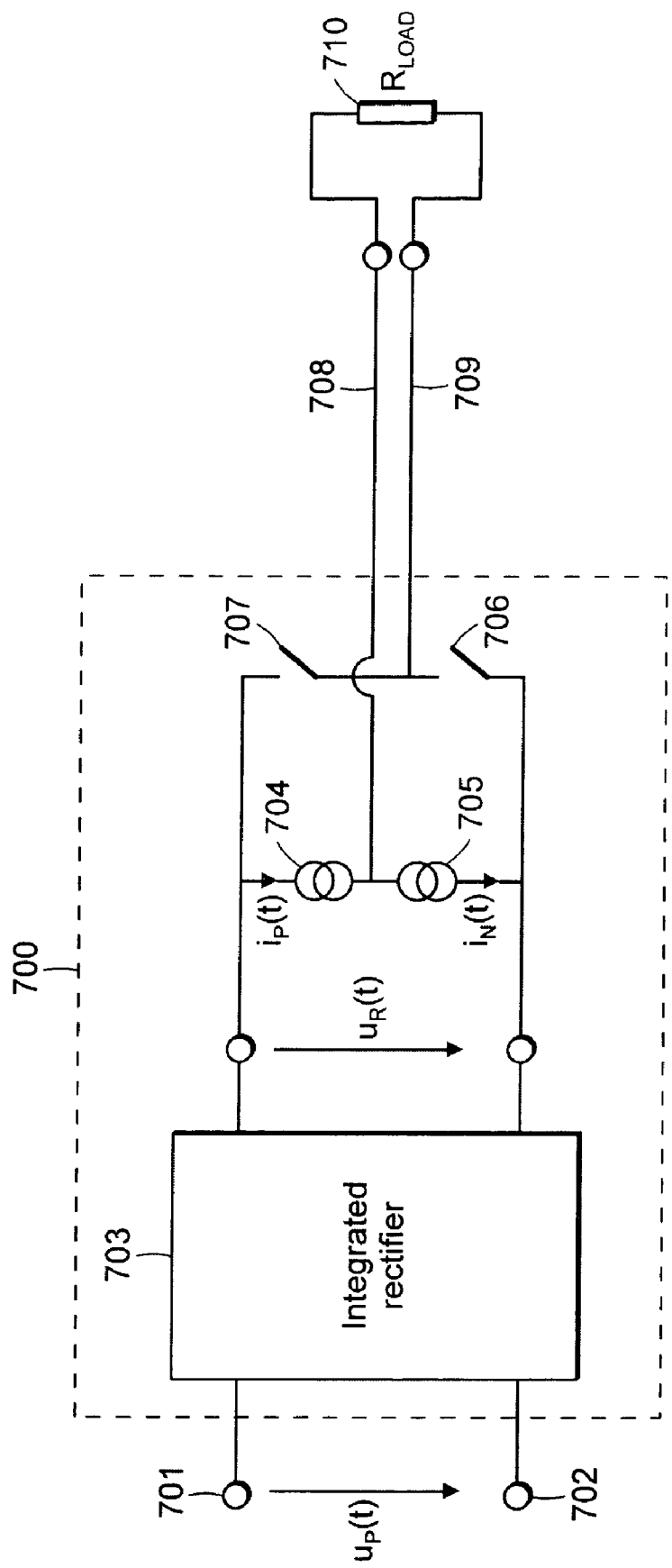
FIG. 7 shows one example of a system for stimulus generation within a single chip processor.

FIG. 7 shows an example of a system for stimulus generation within a single-chip system 700. For convenience, only one stimulation electrode pair 708 and 709 is shown, with the impedance between these electrodes is represented by a resistive element, load resistor 710. The goal is for there to be no dc voltage potential developed between input contacts 701 and 702, or between the stimulation electrode pair 708 and 709. Assuming a dc-free input voltage $u_P(t)$ composed of segments of constant voltages such as the ones shown in FIG. 3, and an integrated rectifier 703 such as the one shown in FIG. 6, then the rectified voltage is $u_R(t) \approx V_{CC}-V_{SS}$, if $u_P(t)$ is non-floating. Stimulation can be achieved with charge-balanced pulses, for example, by generating a symmetrical biphasic pulse. For the first phase, a current amplitude $i_P(t)$ is applied in first current source 704 (e.g., PMOS transistors) and first switch 706 (e.g., an NMOS transistor) is closed. For the second phase, a current amplitude $i_N(t)$ is applied in second current source 705 (e.g., NMOS transistors) and second switch 707 (e.g., a PMOS transistor) is closed. With such a switching procedure, the mean potentials at the electrodes 707 and 708 are $$\frac{V_{CC} - V_{SS}}{2},$$

respectively. Besides it is ensured that the mean potentials at 708/709 are equal to the mean potentials at 701/702, even if the insulation at 701/702 provided, e.g., by some non-hermetic organic material, is not perfect.

In further embodiments, the power supply and the prosthetic processing circuit may be integrated onto one single chip, this chip being encapsulated by some non-hermetic material. The chip itself is protected from body fluids by oxide or nitride layers or some similar material, exposing just the input and output pads, which consequentially consist of some non-corrosive biocompatible metal, such as platinum, iridium, gold, niobium, titanium or tantalum. Thus the whole system consists of a non-hermetically encapsulated single chip, one or more receiver coils to receive power and information signals via some rf-carrier and a set of electrodes.

A number of well known rectification circuits may be used. The capacitors $C_O$ (like the ones in FIG. 2) are integrated chip capacitors, which are somewhat limited in size. To obtain a sufficiently smooth dc-supply, this requires either rf-carriers of sufficiently high frequency or a rectangular-shaped input signal. In the latter case, the inductive transcutaneous transmission system needs to be sufficiently broadband.

Although various exemplary embodiments of the invention have been disclosed, various changes and modifications can be made which will achieve some of the advantages of the invention without departing from the true scope of the invention.

What is claimed is:

1. An implantable electronic system comprising:
   an implantable power supply including:
   i. a plurality of power input ports configured to receive an externally generated power supply signal without developing a dc potential, and
   ii. a plurality of power output ports configured to develop a detected power signal without developing a dc potential; and
   an implantable prosthetic processing module including:
   i. a plurality of prosthetic processing input ports connected to the power output ports and configured to receive the detected power signal without developing a dc potential, and
   ii. a plurality of prosthetic processing output ports configured to develop a prosthetic stimulation signal output without developing a dc potential for electrically stimulating target neural tissue.

2. An implantable electronic system according to claim 1, wherein the power supply is in a non-hermetic, humidity resistant package.

3. An implantable electronic system according to claim 1, wherein the prosthetic processing module is in a non-hermetic, humidity resistant package.

4. An implantable electronic system according to claim 1, wherein the prosthetic processing input ports are connected to the power output ports by wire.

5. An implantable electronic system according to claim 1, wherein at least one of the plurality of ports includes a disconnectable connector to allow wires to be easily attached to and detached from the plurality of ports.

6. An implantable electronic system according to claim 1, wherein the externally generated power supply signal is a radio frequency signal.

7. An implantable electronic system according to claim 1, wherein the externally generated power supply signal is developed by an implanted receiving coil.

8. An implantable electronic system according to claim 1, wherein the externally generated power supply signal contains both energy and information.

9. An implantable prosthesis system including an implantable electronic system according to any of claims 1-8.

10. An implantable prosthesis system according to claim 9, wherein the system is a cochlear prosthesis system.

11. An implantable prosthesis system according to claim 9, wherein the system is a retinal prosthesis system.

* * * * *